(12) United States Patent
Wang et al.

(10) Patent No.: US 6,245,520 B1
(45) Date of Patent: Jun. 12, 2001

(54) METHODS FOR INTRODUCING NUCLEIC ACIDS INTO MAMMALIAN CELLS USING IMIDAZOLIUM LIPIDS

(75) Inventors: Jinkang Wang, San Francisco; Ralph Niven, Redwood City; Yilin Zhang, San Mateo, all of CA (US); Pingzhong Huang, Apex, NC (US)

(73) Assignee: Megabios Corporation, Burlingame, CA (US)

( * ) Notice: Subject to any disclaimer, the term of this patent is extended or adjusted under 35 U.S.C. 154(b) by 0 days.

(21) Appl. No.: 09/626,268

(22) Filed: Jul. 25, 2000

Related U.S. Application Data

(62) Division of application No. 09/183,634, filed on Oct. 30, 1998, now Pat. No. 6,121,457.
(60) Provisional application No. 60/065,859, filed on Nov. 14, 1997.

(51) Int. Cl.[7] .................... A61K 31/4164; C07D 233/14; C07D 233/22; C12Q 1/68; C12P 19/34
(52) U.S. Cl. ..................... 435/6; 435/69.1; 435/70.1; 435/91.1; 435/172.1; 435/320.1; 435/375; 548/349.1; 424/450; 514/44; 514/400
(58) Field of Search ................... 435/6, 69.1, 320.1, 435/375; 548/349.1; 424/450; 514/400, 44

(56) References Cited

U.S. PATENT DOCUMENTS

| | | | |
|---|---|---|---|
| 3,849,435 | 11/1974 | Diery et al. | 260/309.6 |
| 4,362,737 | 12/1982 | Schafer et al. | 424/273 |
| 4,865,614 | 9/1989 | Ploog et al. | 8/115.6 |
| 5,011,937 | 4/1991 | Govindan | 548/354 |
| 5,705,655 | 1/1998 | Heath et al. | 548/350.1 |
| 5,830,878 | 11/1998 | Gorman et al. | 514/44 |
| 6,121,457 | 9/2000 | Wang et al. | 548/350.1 |

FOREIGN PATENT DOCUMENTS 95-14380   6/1995   (WO) ................ 548/350.1

*Primary Examiner*—Floyd D. Higel
(74) *Attorney, Agent, or Firm*—Townsend and Townsend and Crew LLP

(57) ABSTRACT

Methods for introducing nucleic acids into mammalian cells are provided which use imidazolium lipids. The imidazolium lipids have the formula:

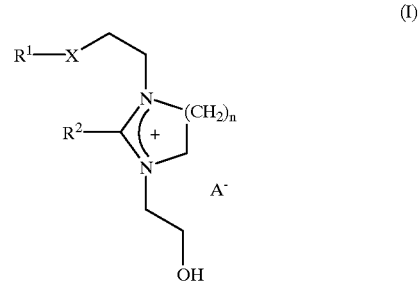

wherein $R^1$ and $R^2$ each independently represent a $C_8$–$C_{24}$ saturated or unsaturated hydrocarbon chain, uninterrupted or interrupted by from 1 to 3 heteroatom moieties selected from —O—, —S—, —NH— and —NR—; X represents —CH$_2$—, —O—, —S—, —NH— or —NR—; wherein R is a lower alkyl group having from 1 to 4 carbon atoms; n is an integer of from 1 to 2; and $A^-$ is an anion.

17 Claims, 2 Drawing Sheets

METHODS FOR INTRODUCING NUCLEIC ACIDS INTO MAMMALIAN CELLS USING IMIDAZOLIUM LIPIDS

This application is a divisional of application Ser No. 09/183,634, filed Oct. 30, 1998, now U.S. Pat No. 6,121,457 which claims priority from Ser. No. 60/065,859 filed Nov. 14, 1997, the disclosures of each being incorporated by reference.

FIELD OF THE INVENTION

This invention relates to novel cationic lipids which contain a five- or six-member nitrogen containing ring and attached fatty acid chains which are stable to hydrolysis. The lipids are useful in the preparation of liposomes and other lipid vesicle carriers of nucleic acids and other substances, for delivery to cells.

BACKGROUND OF THE INVENTION

The introduction of genetic material into a cell can facilitate expression of an encoded protein to complement a deficient or defective protein. The use of such technology allows for the treatment of disease as well as production of certain proteins in an in vitro application.

One method of introducing nucleic acids into a cell is mechanically, using direct microinjection. However this method is labor-intensive and, therefore, only practical for transfecting small numbers of cells such as eukaryotic germline cells for the production of transgenic systems. To be effective in treating a disease, a nucleic acid-based therapy typically must enter many cells.

Gene transfer entails distributing nucleic acids to target cells and then transferring the nucleic acid across a target cell membrane intact and, typically, into the nucleus in a form that can function in a therapeutic manner. In vivo gene transfer is complicated by serum interactions, immune clearance, toxicity and biodistribution, depending on the route of adminstration.

The in vivo gene transfer methods under study in the clinic consist almost entirely of viral vectors. Although viral vectors have the inherent ability to transport nucleic acids across cell membranes and some can integrate exogenous DNA into the chromosomes, they can carry only limited amounts of DNA and also pose risks. One such risk involves the random integration of viral genetic sequences into patient chromosomes, potentially damaging the genome and possibly inducing a malignant transformation. Another risk is that the viral vector may revert to a pathogenic genotype either through mutation or genetic exchange with a wild-type virus.

More recently, cationic lipids have been used to deliver nucleic acids to cells, allowing uptake and expression of foreign genes both in vivo and in vitro. While the mechanism by which cationic lipid carriers act to mediate transfection is not clearly understood, they are postulated to act in a number of ways with respect to both cellular uptake and intracellular trafficking. Some of the proposed mechanisms by which cationic lipids enhance transfection include: (i) compacting the DNA, protecting it from nuclease degradation and enhancing receptor-mediated uptake, (ii) improving association with negatively-charged cellular membranes by giving the complexes a positive charge, (iii) promoting fusion with endosomal membranes facilitating the release of complexes from endosomal compartments, and (iv) enhancing transport from the cytoplasm to the nucleus where DNA may be transcribed. When used for in vivo delivery, the role of the cationic lipid carriers is further complicated by the interactions between the lipid-nucleic acid complexes and host factors, e.g., the effects of the lipids on binding of blood proteins, clearance and/or destabilization of the complexes.

Typically, cationic lipids are mixed with a non-cationic lipid, usually a neutral lipid, and allowed to form stable liposomes, which liposomes are then mixed with the nucleic acid to be delivered. The liposomes may be large unilamellar vesicles (LUVs), multilamellar vesicles (MLVs) or small unilamellar vesicles (SUVs). The liposomes are mixed with nucleic acid in solution, at concentrations and ratios optimized for the target cells to be transfected, to form cationic lipid-nucleic acid transfection complexes. Alterations in the lipid formulation allow preferential delivery of nucleic acids to particular tissues in vivo. PCT patent application numbers WO 96/40962, WO 96/40963. Certain preformed cationic liposome compositions are available, such as LIPOFECTIN® and LIPOFECTAMINE®. Another method of complex formation involves the formation of DNA complexes with mono- or poly-cationic lipids without the presence of a neutral lipid. These complexes are often not stable in water. Additionally, these complexes are adversely affected by serum (see, Behr, *Acc. Chem. Res.* 26:274–78 (1993)). An example of a commercially available poly-cationic lipid is TRANSFECTAM®.

While the use of cationic lipid carriers for transfection is now well established, structure activity relationships are not well understood. It is postulated that different lipid carriers will affect each of the various steps in the transfection process (e.g., condensation, uptake, nuclease protection, endosomal release, nuclear trafficking, and decondensation) with greater or lesser efficiency, thereby making the overall transfection rate difficult to correlate with lipid structures. Thus, alterations in either the cationic or neutral lipid component do not have easily predictable effects on activity. For the most part, therefore, improvements to known cationic lipid-mediated delivery systems are dependent on empirical testing. When intended for in vivo transfection, new lipids and lipid formulations should be screened in vivo to accurately predict optimal lipids and formulations for transfection of target cells.

More recently, new cationic lipids have been prepared which exhibit excellent transfection properties when formulated with nucleic acids. See WO 95/14380, the disclosure of which is incorporated herein by reference. The compositions provided in WO 95/14380 are metabolizable in animal cells to components that are typically endogenous to the cells. Despite the properties associated with the novel cationic lipids, there exists a need for cationic lipids which are more hydrolytically stable and which can be formulated into suitable transfection compositions. The present invention provides such cationic lipids, along with methods for their preparation and use in lipid-based compositions.

Relevant Literature

Cationic lipid carriers have been shown to mediate intracellular delivery of plasmid DNA (Felgner et al., (1987)

Proc. Natl. Acad. Sci. (USA), 84:7413–7416); mRNA (Malone et al., (1989) Proc. Natl. Acad. Sci. (USA) 86:6077–6081); and purified transcription factors (Debs et al., (1990) J. Biol. Chem. 265:10189–10192), in functional form. Literature describing the use of lipids as carriers for DNA include the following: Zhu et al., (1993) Science, 261:209–211; Vigneron et al., (1996) Proc. Natl. Acad. Sci. (USA), 93:9682–9686; Hofland et al., (1996) Proc. Natl. Acad. Sci. (USA), 93:7305–7309; Alton et al., (1993) Nat. Genet. 5:135–142; von der Leyen et al., (1995) Proc. Natl. Acad. Sci. (USA), 92:1137–1141; See also Stribling et al., (1992) Proc. Natl. Acad. Sci (USA) 89:11277–11281, which reports the use of lipids as carriers for aerosol gene delivery to the lungs of mice. For a review of liposomes in gene therapy, see Lasic and Templeton, (1996) Adv. Drug Deliv. Rev. 20:221–266.

The role of helper or neutral lipids in cationic lipid-mediated gene delivery is described in Felgner et al., (1994) J. Biol. Chem. 269(4): 2550–2561 (describing improved transfection using DOPE); and Hui et al., (1996) Biophys. J. 71: 590–599. The effect of cholesterol on liposomes in vivo is described in Semple et al., (1996) Biochem. 35(8): 2521–2525.

SUMMARY OF THE INVENTION

In one aspect, the present invention provides compounds having the formula:

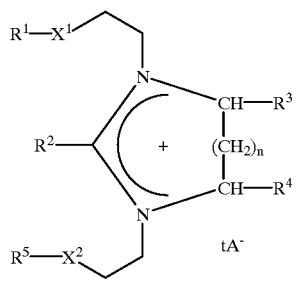

The symbols in this formula have the following meanings:
$R^1$ and $R^2$ each independently represent a $C_8$–$C_{24}$ saturated or unsaturated hydrocarbon, alkyl or acyl, chain, which is optionally interrupted by from 1 to 3 heteroatom moieties, such as —O—, —S—, —NH— and —$NR^6$—;
$R^3$ and $R^4$ each independently represent H or a $C_1$–$C_5$ saturated or unsaturated hydrocarbon chain;
$X^1$ represents —$CH_2$—, —O—, —S—, —NH— or —$NR^7$—;
$X^2$ represents —$CH_2$—, —O—, —S—, —NH— or —$NR^8$—;
$R^5$ represents H, $R^9$ or —$(CH_2)_m$—Y;
Y represents —OH, —$NH_2$, —$NHR^{10}$ or —$NR^{11}R^{12}$;
$R^6$, $R^7$, $R^8$, $R^9$, $R^{10}$, $R^{11}$ and $R^{12}$ each independently represent an alkyl or acyl group having from 1 to 4 carbon atoms;
m represents an integer from 1 to 5;
n represents 0 or 1;
$A^-$ represents an anion, preferably chloride or citrate; and
t is an integer equal to the number of positive charges borne by the molecule.

In compounds according to Formula (I), wherein one or more of $R^1$, $R^2$, $X^1$, $X^2$ and/or Y comprise an amine group, one or more of the amine groups can be a quaternary amine group. Quaternization can be effected by protonation or other mechanisms known in the art.

In another aspect, the present invention provides lipid vesicle compositions which comprise a compound of the formula provided above.

In yet another aspect, the present invention provides lipid:nucleic acid complexes which comprise a nucleic acid, typically as DNA, and a compound of Formula (I), above.

In still another aspect, the present invention provides a method for transfecting mammalian cells, comprising contacting the cells with a composition comprising an expression cassette and a compound of Formula (I), (II), or (III).

DETAILED DESCRIPTION OF THE INVENTION

Abbreviations

Figure 1:
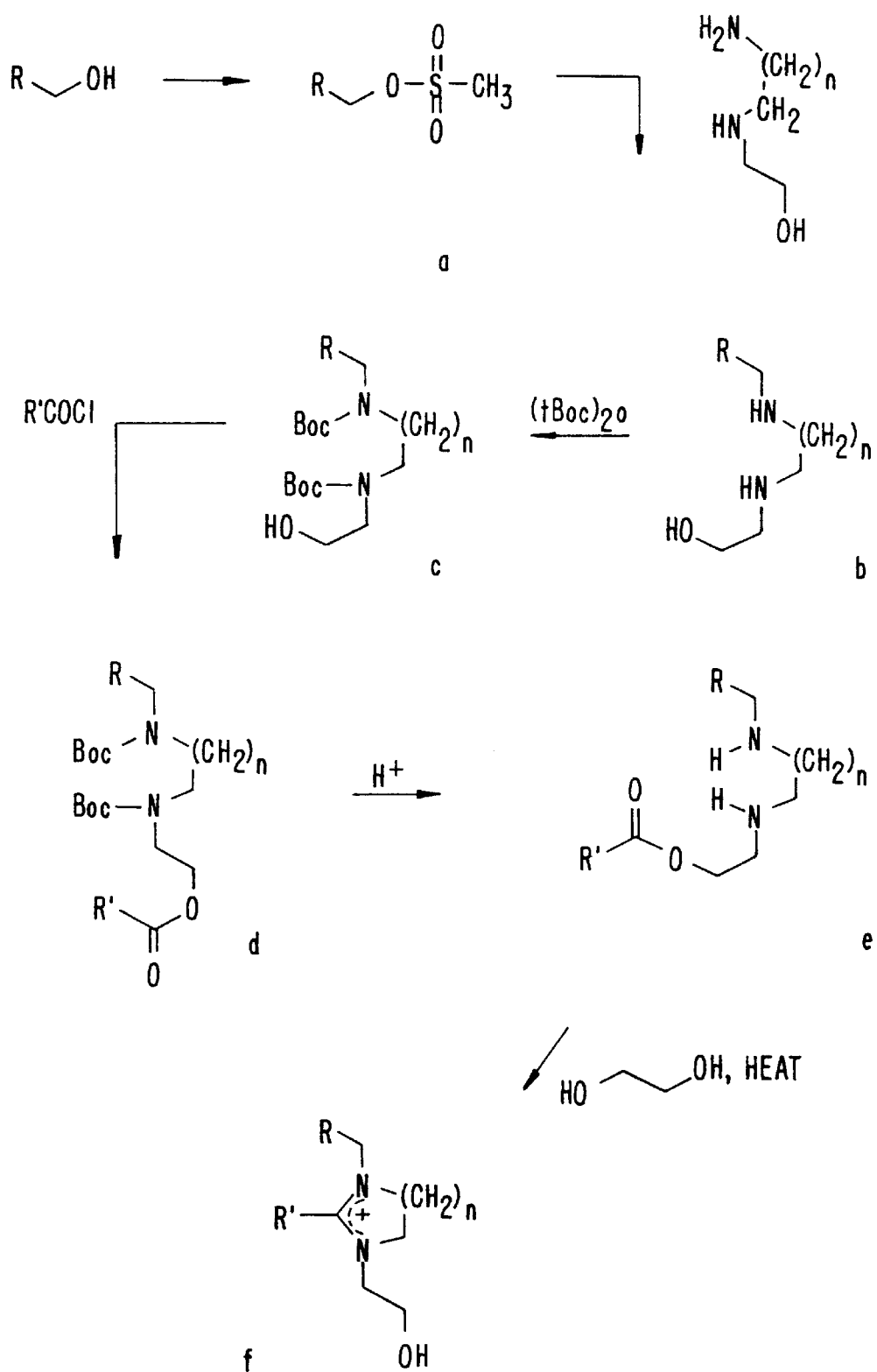
FIG. 1 provides a synthesis scheme for a compound of Formula (I) in which $X^1$ is —$CH_2$—, $X^2$ is —O— and $R^5$ is H.

The abbreviations used herein have the following meanings: DOTIM, 1-[2-(9(z))-octadecenoyloxy)ethyl]-2-(8(z)-heptadecenoyl0-3-(2-hydroxyethyl)imidazolinium chloride; EDTA, ethylenediaminetetraacetic acid; CAT, chloramphenicol aminotransferase; D5W, 5% dextrose in water; HCMV, human cytomegalovirus; CHOL, cholesterol; DLPE, dilauroylphosphatidylethanolamine; IV, intravenous; CBC, complete blood count;

Embodiments of the Invention

Compounds

As noted in the Summary, the present invention provides novel cationic lipids which are hydrolytically stable. As a result, these lipids are useful in the preparation of lipid vesicle carriers, or lipid-nucleic acid complexes which are used for transfection of cells.

The cationic lipids of the present invention are represented by Formula (I):

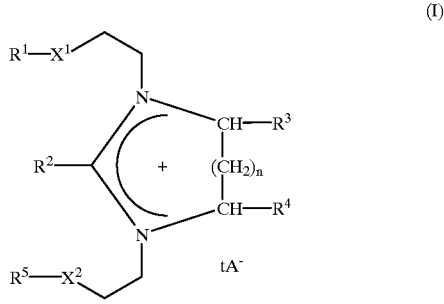

In this formula, $R^1$ and $R^2$ each independently represent a $C_8$–$C_{24}$ saturated or unsaturated hydrocarbon chain, which is optionally interrupted by from 1 to 3 heteroatom moieties, such as —O—, —S—, —NH— and —NR—. In preferred embodiments, $R^1$ and $R^2$ each independently represent a $C_8$–$C_{24}$ saturated or unsaturated hydrocarbon chain. Examples of suitable saturated hydrocarbon chains include those chains derived from fatty acids or alcohols, for example, lauryl (C12:0), myristyl (C14:0), palmityl (C16:0), stearyl (C18:0), arachidyl (C20:0), and behenyl (C22:0). Examples of suitable unsaturated hydrocarbon chains include, for example, oleyl (C18:1,cis-9), linoleyl (C18:2, cis-9,12), elaidyl (C18:1,trans-9), linolelaidyl (C18:2,trans-9,12), eicosenyl (C20:1,cis-11), and the like. In each of the above, the configuration is provided as, for example, (C20:1, cis-11), indicating a twenty carbon chain having a single cis double bond between the eleventh and twelfth carbon atoms (when counting the carbon atoms in the conventional manner for fatty acids). While examples are provided for saturated and unsaturated hydrocarbon chains having an even number of carbon atoms, the invention is not so limited. A variety of methods are available to the skilled chemist for a one-carbon homologation or degradation to provide hydrocarbon chains having an odd number of carbon atoms. Additionally, due to the synthetic scheme provided in FIG. 1 and discussed below, $R^2$ will have an odd number of carbon atoms when synthesis is carried out using commercially available fatty acids such as oleic acid, myristic acid, palmitic acid, and the like. Still further, $R^1$ will typically have an odd number of carbon atoms when synthesis (according to FIG. 1) is carried out beginning with a fatty alcohol having an even number of carbon atoms (to produce compounds of Formula (I) in which X is —$CH_2$—).

In one group of preferred embodiments, $R^1$ and $R^2$ will each independently be a $C_{12}$–$C_{20}$ saturated hydrocarbon chain. In another group of preferred embodiments $R^1$ and $R^2$ will each independently be a $C_{12}$–$C_{20}$ unsaturated hydrocarbon chain. Particularly preferred embodiments, within the group of unsaturated hydrocarbon chains, are those which contain a single double bond in the cis orientation (e.g., oleyl, elaidyl, and those having one more or one less carbon atoms).

$R^3$ and $R^4$ are each independently H or a $C_1$–$C_5$ saturated or unsaturated hydrocarbon chain. Examples of hydrocarbon chains having from 1 to 5 carbon atoms include, but are not limited to, methyl, ethyl, propyl, cyclopropyl, isopropyl, n-butyl, i-butyl, t-butyl, pentyl, cyclopentyl, cis-2-pentene, trans-2-pentene and the like.

In some embodiments, various groups, known to those of skill in the art, may be added to the compounds to enhance properties such as water solubility, targetting of particular cell surfaces, or fusogenicity. For example, poly (ethyleneglycol) can be attached to a hydroxyl group at $R_5$.

In Formula (I) above, $X^1$ represents a linking group such as —$CH_2$—, —O—, —S—, —NH— or —$NR^7$—. Preferably, X is —$CH_2$— or —O—, more preferably —$CH_2$—.

The compounds of the invention comprise both 5- and 6-membered ring heterocycles. Thus, the subscript n in Formula (I) is either 0 or 1, preferably, 0. Additionally, the dashed arc and + sign within the nitrogen heterocycle are meant to indicate the presence of a double bond between either of the nitrogen atoms in the ring and the single carbon atom which joins the two nitrogen atoms. As a result, a positive charge (+) is associated with one or the other of the nitrogen atoms, depending on the position of the double bond (i.e., the positive charge is associated with the nitrogen atom which forms one end of the double bond).

$X^2$ is a linking group which is either —$CH_2$—, —O—, —S—, —NH— or —$NR^8$—. Preferably, X is —$CH_2$— or —O—, more preferably —O—.

$R^5$ is H, $R^9$ or —$(CH_2)_m$—Y, preferably H.

Y is —OH, or an amino or alkylamino group such as —$NH_2$, —$NHR^{10}$, —$NR^{11}R^{12}$, preferably —OH.

The alkyl substituents on the amino groups, $R^6$, $R^7$, $R^8$, $R^9$, $R^{10}$, $R^{11}$ and $R^{12}$, each independently represent an alkyl group having from 1 to 4 carbon atoms. Examples of hydrocarbon chains having from 1 to 4 carbon atoms include, but are not limited to, methyl, ethyl, propyl, cyclopropyl, isopropyl, n-butyl, i-butyl, t-butyl and cyclobutyl. The alkyl groups can be either saturated or unsturated. In preferred embodiments, the alkyl groups are methyl or ethyl, more prefereably methyl. In addition, in some embodiments, these amines can be quaternized for example, by methylation.

The symbol A— represents an anion, preferably a pharmaceutically acceptable anion. As used herein, the term "pharmaceutically acceptable anion" refers to anions of organic and inorganic acids which provide non-toxic salts in pharmaceutical preparations. Examples of such anions include, but are not limited to, chloride, bromide, sulfate, phosphate, acetate, benzoate, citrate, glutamate, and lactate. The preparation of pharmaceutically acceptable salts is described in Berge, et al., *J Pharm. Sci.* 66:1–19 (1977), incorporated herein by reference. Preferably, A— is chloride, bromide or citrate.

In one group of particularly preferred embodiments, $R^1$ and $R^2$ each independently represent a $C_{12}$–$C_{18}$ unsaturated hydrocarbon chain, $X^1$ is —O—, $X^2$ is —OH or —$(CH_2)_2$—OH and n is 0. In another group of particularly preferred embodiments, $R^1$ represents a $C_{18}$-unsaturated hydrocarbon chain, $R^2$ represents a $C_{17}$ unsaturated hydrocarbon chain, $X^1$ is —O—, $X^2$ is —OH and n is 0.

In another group of particularly preferred embodiments, $X^1$ is —$CH_2$—. Within this group of embodiments, $R^1$ will preferably have an odd number of carbon atoms and contain one double bond having a cis configuration. Also preferred are those embodiments in which $R^2$ is a saturated hydrocarbon chain having an odd number of carbon atoms, or an unsaturated hydrocarbon chain having an odd number of carbon atoms with one double bond having a cis configuration. Most preferred in this group of embodiments are the compounds of Formulas (II) and (III).

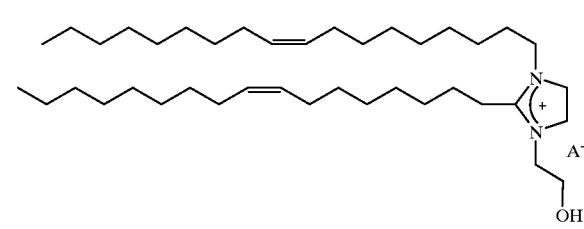

(II)

-continued

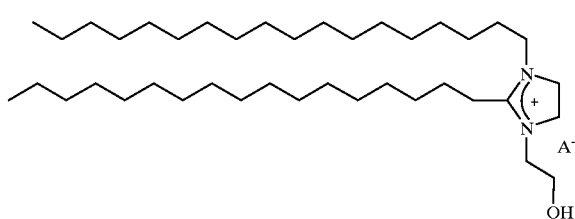

(III)

Preparation of the Imidazolinium Lipids

Preparation of lipids of Formula (I) can be carried out according to the outline provided in FIG. 1. Briefly, a fatty alcohol is converted to a sulfonate ester (an activated leaving group) by treatment with, for example, methanesulfonyl chloride or p-toluenesulfonyl chloride to provide a compound a. Reaction of compound a with 2-(2-aminoethylamino)ethanol provides compound b. Protection of each of the amino groups as their t-butyl carbamate can be accomplished with reagents such as (t-Boc)$_2$O or BOC-ON (from Aldrich Chemical Co., Milwaukee, Wis., USA) to provide compound c. Following protection of the amino groups, the hydroxyl group can be acylated with an appropriate acid chloride, typically a fatty acid chloride to provide compound d which is then deprotected to provide compound e. Heating compound e in a suitable polar solvent (e.g., ethylene glycol) produces an imidazolinium ring (or the related six-member ring) with concomitant loss of water, and provides target compound f. As can be seen from FIG. 1, the limitations on $R^1$ and $R^2$ in Formula (I) will depend only on the availability of fatty alcohols and fatty acids. Accordingly, compounds of Formula (I) are readily formed in which $R^2$ has an odd number of carbon atoms, optionally with one or more sites of unsaturation. Similarly, for those compounds of Formula (I) in which X is —CH$_2$—, $R^1$ will have an odd number of carbon atoms when the starting material is one of the readily available fatty alcohols (e.g., stearyl alcohol and oleyl alcohol). Preparation of compounds in which $R^1$ or $R^2$ have an even number of carbon atoms can be accomplished by suitable conversion of the starting fatty acids or alcohols to their longer or shorter homologs. Additionally, position and geometry (cis or trans) of any double bonds present can also be altered in the starting materials using known methods for isomerization of double bonds as well as positional transfer of double bonds.

The salt formed using the procedures in FIG. 1 is a chloride salt. Replacement of the chloride ion with another anion can be accomplished using, for example, ion exchange resins which are equilibrated with the desired anion.

Figure 2:
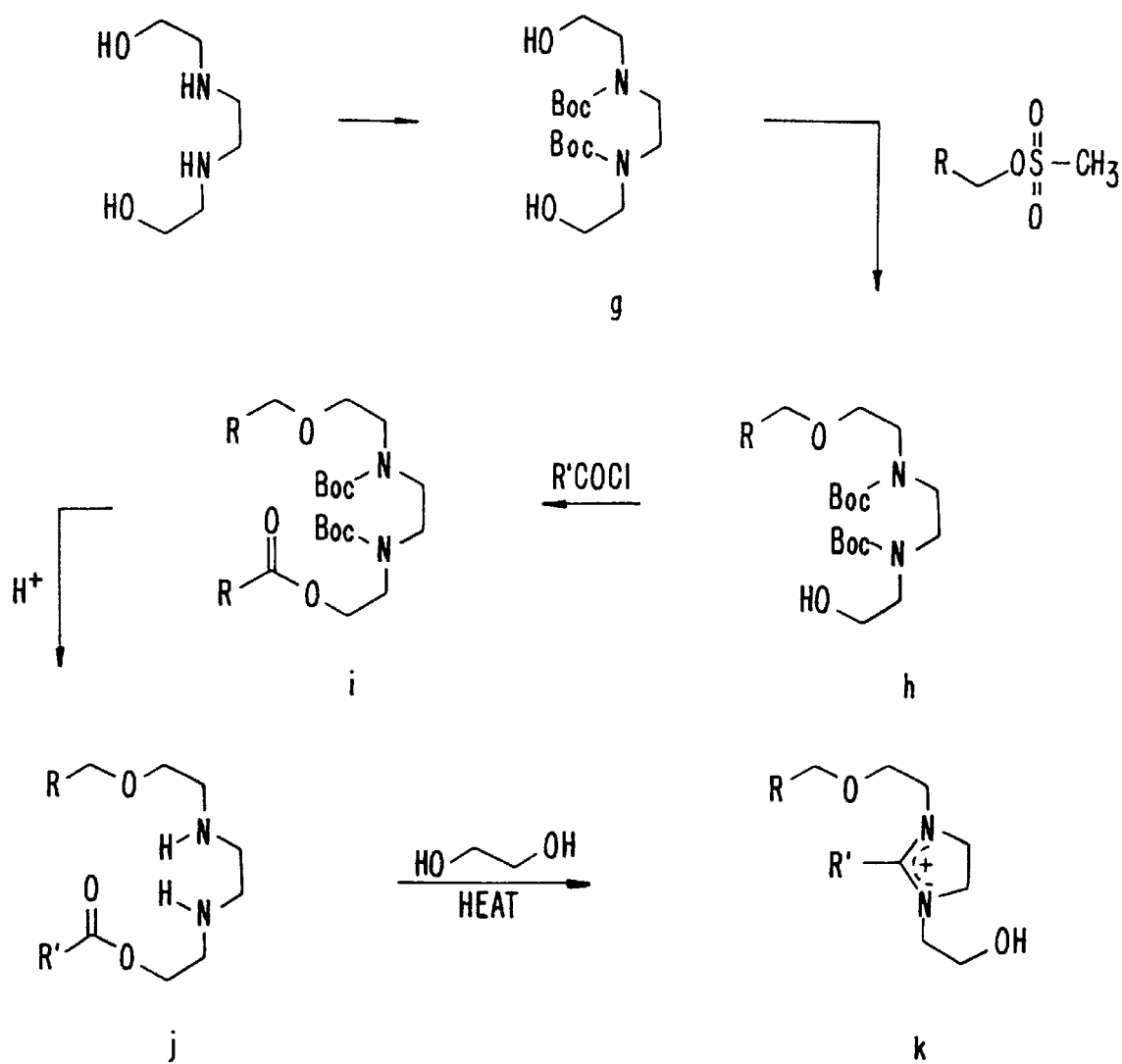
FIG. 2 provides a synthesis scheme for a compound of Formula (I) in which $X^1$ and $X^2$ are —O— and $R^5$ is H.

Other compounds of Formula (I) can be prepared by methods outlined in FIG. 2. As outlined in FIG. 2, compounds of Formula (I) in which X is —O— can be prepared from fatty alcohols, fatty acids, and N,N'-di(2-hydroxyethyl)-ethylene diamine. Briefly, the amino groups of N,N'-di(2-hydroxyethyl)-ethylene diamine are protected as their Boc carbamates to provide compound g, which is then monoalkylated with an activated fatty alcohol sulfonate ester (compound a) to form compound h. Acylation of the remaining alcohol moiety is accomplished by treatment of compound h with a fatty acid chloride to provide compound i. Conversion of compound i to target compound k is carried out by first removing the Boc protecting groups then heating the resultant compound j in a polar solvent to effect the cyclization to compound k.

Lipid Vesicle Compositions

In another aspect, the present invention provides lipid vesicle compositions which contain a lipid of Formula (I), above. The lipid vesicle compositions will typically be in the form of liposomes (e.g., unilammelar vesicles, multilammelar vesicles), or other lipid bilayer forms. The cationic lipids described above can be used alone or combined with other lipids in the preparation of compositions useful in intracellular delivery systems (e.g., transfection systems), or other conventional drug delivery systems.

A variety of other lipids are suitable for use in the present compositions. As used herein, the term "lipid" refers to any suitable material resulting in a bilayer in aqueous solution such that a hydrophobic portion of the lipid material orients toward the bilayer while a hydrophilic portion orients toward the aqueous phase. Hydrophilic characteristics derive from the presence of phosphate, carboxylic, sulfato, amino, sulfhydryl, nitro, and other like groups. Hydrophobicity is conferred by the inclusion of groups that include, but are not limited to, long chain saturated and unsaturated aliphatic hydrocarbon groups, with such groups being optionally substituted by one or more aromatic, cycloaliphatic or the preferred lipids for use in conjunction with the cationic lipids of Formula (I) are phosphoglycerides, sphingolipids and sterols (e.g. cholesterol), representative examples of which include diacyl derivatives of phosphatidylcholine, phosphatidylethanolamine, phosphatidylserine, phosphatidylinositol and phosphatidic acid (e.g., palmitoyloleoyl phosphatidylcholine, dipalmitoylphosphatidylcholine, dioleoylphosphatidylcholine, distearoylphosphatidylcholine and dilinoleoylphosphatidylcholine) and the related lyso-phosphatidylcholine and lysophosphatidylethanolamine. Still other lipids are useful, such as sphingolipid and glycosphingolipid families. Additionally, the lipids described above may be mixed with other lipids (co-lipids) including triglycerides and sterols (e.g., cholesterol).

When the lipid vesicle compositions are in the form of liposomes, the compounds of Formula (I) will typically be combined with other lipids, including neutral lipids, zwitterionic lipids, anionic lipids or other cationic lipids known to those of skill in the art. Preferably, the compositions will comprise other neutral lipids or zwitterionic lipids (e.g., cholesterol, dilaurylphosphatidylethanolamine). Particularly preferred co-lipids include DOPE, DLPE and cholesterol. For systemic delivery of nucleic acids, cholesterol is the preferred co-lipid.

In general, less saturated lipids are more easily sized, particularly when the liposomes must be sized below about 0.3 microns. In one group of embodiments, lipids containing saturated fatty acids with carbon chain lengths in the range of $C_{14}$ to $C_{22}$ are preferred. In another group of embodiments, lipids with mono- or di-unsaturated fatty acids with carbon chain lengths in the range of $C_{14}$ to $C_{22}$ are used. Additionally, lipids having mixtures of saturated and unsaturated fatty acid chains can be used.

A number of methods are available for preparing liposome compositions (see, for example, Szoka et al., *Ann. Rev. Biophys. Bioeng.* 9:467 (1980), U.S. Pat. Nos. 4,235,871, 4,501,728, 4,837,028, the text Liposomes, Marc J. Ostro, ed., Marcel Dekker, Inc., New York, 1983, Chapter 1, and Hope, et al., *Chem. Phys. Lip.* 40:89 (1986), all of which are incorporated herein by reference). One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions.

Following liposome preparation, the liposomes may be sized, for example, by extrusion, sonication, filtration or emulsification to achieve a desired size range and a relatively narrow distribution of liposome sizes, which is particularly desirable for in vivo delivery of nucleic acids. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Techniques for sizing liposomes to a desired size, include sonication (see, U.S. Pat. No. 4,737,323, incorporated herein by reference), extrusion through small-pore polycarbonate membranes or an asymmetric ceramic membrane, and homogenization. Homogenization relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In any of the methods, the liposome size distribution can be monitored by conventional dynamic laser light scattering.

The lipid vesicle compositions will, in some embodiments, have an attached targeting moiety. For example, a ligand binding specifically to a receptor on a particular target cell type can be used to target delivery of the lipid carrier (with, e.g., the DNA or antibiotic of interest) to the desired target cells. Alternatively, the active compound may be a peptide or other small molecule designed to regulate intracellular trafficking of the delivered substance, e.g., triggering endosomal release or transport into the nucleus using a nuclear localizing sequence.

The active compounds bound to the lipid mixture can vary widely, from small haptens (molecular weights of about 125 to 2000) to antigens (molecular weights ranging from around 6000 to 1 million). Of particular interest are proteinaceous ligands that bind to and are internalized by specific complementary binding partners on cell surfaces. Illustrative active compounds include cytokines, interferons, hormones, asialeglycoprotein antibodies to cell surface receptors or other molecules, and fragments of such compounds that retain the ability to bind to the same cell surface binding partners that bind the original (non-fragment) molecules.

The number of active compounds bound to a lipid carrier will vary with the size of the complex, the size of the compound, the binding affinity of the molecule to the target cell receptor or ligand, and the like. Usually, the bound active molecules will be present in the lipid mixture in from about 0.001 to 10 mole percent, more usually from about 0.01 to 5 mole percent based on the percent of bound molecules to the total number of molecules available in the mixture for binding.

Lipid-Nucleic Acid Compositions

In another aspect, the present invention provides lipid-nucleic acid compositions in which the lipid portion comprises at least one cationic lipid of Formula (I). Preferably, the cationic lipids of Formula (I) are those in which X is —$CH_2$—. Other preferred embodiments for the cationic lipid and, optionally, co-lipids are as described above.

The nucleic acids which are useful in the present invention are typically nucleotide polymers having from 10 to 100,000 nucleotide residues. Typically, the nucleic acids are to be administered to a subject for the purpose of replacing or enhancing the expression of a cellular protein and may also encode an RNA molecule, e.g. antisense RNA or ribozyme, which will inhibit an undesired cellular activity, e.g. in a virus-infected cell or tumor cell. Additionally, the nucleic acid can carry a label (e.g., radioactive label, fluorescent label or calorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, mRNA or oligonucleotides containing nucleic acid analogs, for example, the antisense derivatives described in a review by Stein, et al., *Science* 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleotide polymers can be single-stranded DNA or RNA, or double-stranded DNA or DNA-RNA hybrids. Examples of double-stranded DNA include structural genes including control and termination regions, and self-replicating systems such as plasmid DNA.

Single-stranded nucleic acids include antisense oligonucleotides (complementary to DNA or RNA), ribozymes and triplex-forming oligonucleotides. In order to increase stability, some single-stranded nucleic acids will preferably have some or all of the nucleotide linkages substituted with stable, non-phosphodiester linkages, including, for example, phosphorothioate, phosphorodithioate, phosphoroselenate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can also be used in the present methods. Thus, the sequences for different proteins may be located on the same or separate plasmids. The gene of interest will be linked to appropriate regulatory elements to provide constitutive or inducible expression and/or tissue specific expression. Additional elements such as antibiotic-sensitive or nutrient-sensitive regions, may be included as required. Non-coding sequences may also be present for various purposes including, for example, regulatory elements to achieve appropriate expression or replication in host cells, or to provide convenient cloning sites.

The nucleic acids used in the present invention can be isolated from natural sources, obtained from such sources as ATCC or GenBank libraries or prepared by synthetic methods. Typically, the nucleic acids will be plasmid DNA, which can be grown and purified in large quantities from bacterial cells.

Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al, chapter 4, in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

The compositions in this aspect of the invention can be in the form of liposome-encapsulated nucleic acids, lipid-bilayer coated nucleic acids, or complexes formed between lipids and nucleic acids.

Preparation of Lipid-Nucleic Acid Compositions

Various lipid-nucleic acid compositions, wherein the lipid portion is typically in the form of liposomes, can be prepared using methods well known in the art. Still other compositions are contemplated by the present invention such as those which are described as lipid particles in WO 96/40964, the disclosure of which is incorporated herein by reference.

For those compositions in which the lipid portion is in the form of liposomes, the lipid vesicle can be prepared by standard methods such as those described above. The resulting liposomes are mixed with a nucleic acid solution with constant agitation to form the cationic lipid-nucleic acid transfection complexes. The preferred size will vary depending on use. For example, smaller transfection complexes are preferred for aerosol administration, thereby reducing shear caused by the aerosolization process. Preferred transfection complex size for aerosol administration is less than 5000 nm, most preferably from 50 to 300 nm. Preferred transfection complex size for intravenous administration is from 50 to 5000 nm, most preferably from 100 to 700 nm. Cationic lipid-nucleic acid transfection complexes can be prepared in various formulations depending on the target cells to be transfected. See, e.g., WO 96/40962 and WO 96/40963. Helper lipids used in these compositions can be substituted and evaluated for concentration, DNA-lipid ratio, etc. For example, if DLPE is substituted for cholesterol, resulting in changes in the physical characteristics of the lipid carrier, it is preferred that additional formulations be tested empirically to obtain optimal results. While a range of lipid-nucleic acid complex formulations will be effective in cell transfection, optimum conditions are determined empirically in the desired experimental system. Lipid carrier compositions may be evaluated by their ability to deliver a reporter gene (e.g. CAT which encodes chloramphenicol acetyltransferase, luciferase, or β-galactosidase) in vitro, or in vivo to a given tissue in an animal, such as a mouse.

For in vitro transfections, the various combinations are tested for their ability to transfect target cells using standard molecular biology techniques to determine DNA uptake, RNA and/or protein production. Typically, in vitro cell transfection involves mixing nucleic acid and lipid, in cell culture media, and allowing the lipid-nucleic acid transfection complexes to form for about 10 to 15 minutes at room temperature. The transfection complexes are added to the cells and incubated at 37° C. for about four hours. The complex-containing media is removed and replaced with fresh media, and the cells incubated for an additional 24 to 48 hours.

In vivo, particular cells can be preferentially transfected, depending on the route of administration, by the use of particular cationic lipids for preparation of the lipid carriers, or by altering the cationic lipid-nucleic acid formulation to preferentially transfect the desired cell types (WO 96/40962). Thus, for example, in circumstances where a negatively charged complex is desired, relatively less cationic lipid will be complexed to the nucleic acid resulting in a higher nucleic acid: cationic lipid ratio. Conversely, in circumstances where a positively charged complex is desired, relatively more cationic lipid will be complexed with the nucleic acid, resulting in a lower nucleic acid: cationic lipid ratio. To avoid precipitation, which generally occurs around charge neutrality, net positively charged complexes are generally prepared by adding nucleic acid to the liposomes, and net negatively charged complexes are prepared by adding liposomes to the nucleic acid, in either case with constant agitation.

The lipid mixtures are complexed with DNA in different ratios depending on the target cell type, generally ranging from about 6:1 to 1:20 µg DNA:nmole cationic lipid. For transfection of airway epithelial cells, e.g., via aerosol, intratracheal or intranasal administration, net negatively charged complexes are preferred. Thus, preferred DNA:cationic lipid ratios are from about 10:1 to about 1:20, preferably about 3:1. For intravenous administration, preferred DNA:cationic lipid ratios range from about 1:3.5 to about 1:20 µg DNA: nmole cationic lipid, most preferably, about 1:6 to about 1:15 µg DNA: nmole cationic lipid. Additional parameters such as nucleic acid concentration, buffer type and concentration, etc., will have an effect on transfection efficiency, and can be optimized by routine experimentation by a person of ordinary skill in the art. Preferred conditions are described in the Examples that follow.

Non-lipid material, (such as biological molecules being delivered to an animal or plant cell or target-specific moieties) can be conjugated to the lipid carriers through a linking group to one or more hydrophobic groups, e.g., using alkyl chains containing from about 12 to 20 carbon atoms, either prior or subsequent to vesicle formation. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, as the literature provides a great variety of such methods. Alternatively, some compounds will have hydrophobic regions or domains which will allow their association with the lipid mixture without covalent linking to one or more lipid groups.

Administration of Lipid-Nucleic Acid Compositions to a Host

Following formation of the lipid-nucleic acid compositions, the compositions (or complexes) can be contacted with the cells to be transfected. Contact between the cells and the lipid-nucleic acid complexes, when carried out in vitro, will take place in a biologically compatible medium. The concentration of complexes can vary widely depending on the particular application, but is generally between about 1 $\mu$mol and about 10 mmol. Treatment of the cells with the lipid-nucleic acid complexes will generally be carried out at physiological temperatures (about 37° C.) for periods of time of from about 1 to 48 hours, preferably of from about 2 to 4 hours. For in vitro applications, the delivery of nucleic acids can be to any cell grown in culture, including primary cell and immortalized cell lines, whether of plant or animal origin, vertebrate or invertebrate, and of any tissue or type. In preferred embodiments, the cells will be animal cells, more preferably mammalian cells, and most preferably human cells.

In one group of preferred in vitro embodiments, a lipid-nucleic acid composition suspension is added to 60–80% confluent plated cells. The concentration of the suspension added to the cells is preferably of from about 0.01 to 0.2 $\mu$g/mL, more preferably about 0.1 $\mu$g/mL.

Typical applications include using well known transfection procedures to provide intracellular delivery of DNA or mRNA sequences which code for therapeutically useful polypeptides. However, the compositions can also be used for the delivery of the expressed gene product or protein itself. In this manner, therapy is provided for genetic diseases by supplying deficient or absent gene products (i.e., for Duchenne's dystrophy, see Kunkel, et al., *Brit. Med. Bull.* 45(3)$_2$630–643 (1989), and for cystic fibrosis, see Goodfellow, *Nature* 341:102–103 (1989)). Other uses for the compositions of the present invention include introduction of antisense oligonucleotides in cells (see, Bennett, et al., *Mol. Pharm.* 41:1023–1033 (1992)).

The compositions of the present invention can also be used for the transfection of cells in vivo, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes.

In one group of embodiments, the in vivo administration of the pharmaceutical compositions is carried out parenterally, e.g., intraarticularly, intravenously, intraperitoneally, subcutaneously, or intramuscularly. More preferably, the pharmaceutical compositions are administered intravenously by a bolus injection for delivery to vascular endothelial cells, by intraperitomal injection for delivery to peritoneal macrophages or cells lining the peritoneal cavity, or by intramuscular or subcutaneous injection for delivery to antigen-presenting cells for purposes of eliciting an immune response. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., *Biotechniques* 6:682–690 (1988); Nicolau, et al., *Crit. Rev. Ther. Drug Carrier Syst.* 6:239–271 (1989), and Behr, *Acc. Chem. Res.* 26:274–278 (1993).

In other embodiments, the pharmaceutical preparations described herein may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue, for example, heart tissue and/or associated vasculature may be transfected with a gene of interest in conjunction with heart surgery, as an adjunct therapy. "Closed" procedures are invasive procedures in which the internal target tissues are not directly visualized, but accessed via inserting instruments through small wounds in the skin. For example, the preparations may be administered to the peritoneum by needle lavage or to the vasculature using a balloon catheter. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

In yet other embodiments, the lipid-nucleic acid complexes can be administered in an aerosol inhaled into the lungs (see, U.S. Pat. No. 5,641,662). For a general review of applicable techniques, see Culver, HUMAN GENE THERAPY, MaryAnn Liebert, Inc., Publishers, New York. pp.70–71 (1994).

The methods of the present invention may be practiced in a variety of hosts. Preferred hosts include mammalian species, such as humans, non-human primates, dogs, cats, cattle, horses, sheep, and the like.

The invention will be better understood in light of the following specific examples, which are merely illustrative and should not be construed as limiting the invention in any respect, as will be evident to those skilled in the art.

EXAMPLES

All of the reagents were purchased from Aldrich Chemical Company (Milwaukee, Wis., USA), except oleyl alcohol and oleoyl chloride, which were obtained from Nu-Chek-Prep, Inc. (Elysian, Minn., USA). All solvents were purchased from Fisher Scientific.

Example 1

This example illustrates the preparation of Compound 1 according to the general scheme outlined in FIG. 1.

(Compound 1)

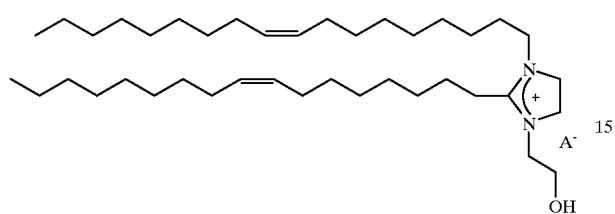

1.1 Oleyl methanesulfoante (compound 1a)

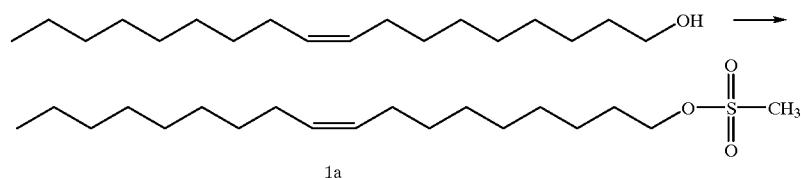

To a mixture of oleyl alcohol (10 g, 37.2 mmol) and pyridine (13.4 mL) in $CH_2Cl_2$ (150 mL), $MeSO_2Cl$ (4.35 ml, 56.2 mmol) was added in 40 min. The mixture was stirred at 0° C. for 40 minutes and then room temperature for 4 h. Ice-water (60 mL) and $Et_2O$ (100 mL) were added and shaken. The organic layer was washed with 0.5 N HCl (2×100 mL), $H_2O$ (100 mL), 0.5 N $NaHCO_3$ (2×50 mL), $H_2O$ (50 mL) and NaCl (50 mL), and dried over $MgSO_4$. Evaporation under reduced pressure gave 12 g (93.0%) of oleyl methanesulfonate 1a as a liquid. $^1H$ NMR ($CDCl_3$): δ0.81 (t, J=7, 3H), 1.22 (m, 22H), 1.67 (m, 2H), 1.93 (m, 4H), (s, 3H), 4.16 (t, J=7, 2H), 5.28 (m, 2H).

1.2 N-(2-Hydroxyethyl)-N'-oleyl-ethylenediamine (compound 1b)

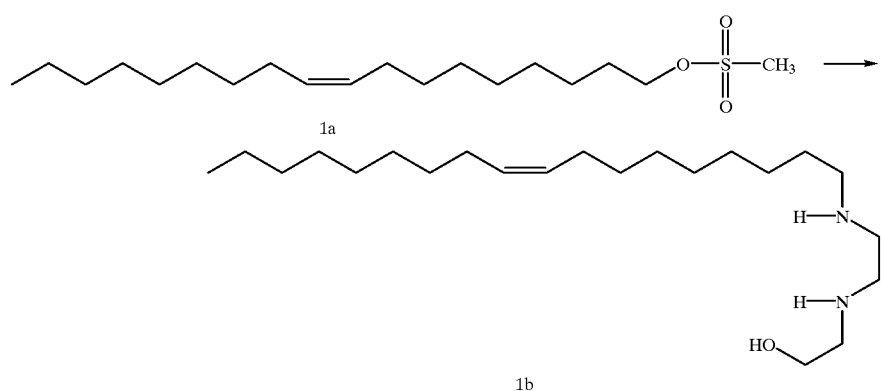

A mixture of oleyl methanesulfonate (7.01 g, 20.3 mmol) and 2-(2-aminoethylamino) ethanol (21.81 g, 209.7 mmol) was heated at 50° C. for 1.5 h. After cooling to room temperature, 30 mL of NaOH solution (10%) was added, stirred for 30 minutes, and extracted with $Et_2O$ (100 ml). The $Et_2O$ solution was washed with $H_2O$ (3× 50 mL) and NaCl solution, dried over $MgSO_4$ and evaporated under reduced pressure to give 8.41 g of the crude product 1b which was used for the next step reaction without further purification.

1.3 N,N'-Di-t-Boc-N-(2-Hydroxyethyl)-N'-oleyl-ethylenediamine (compound 1c)

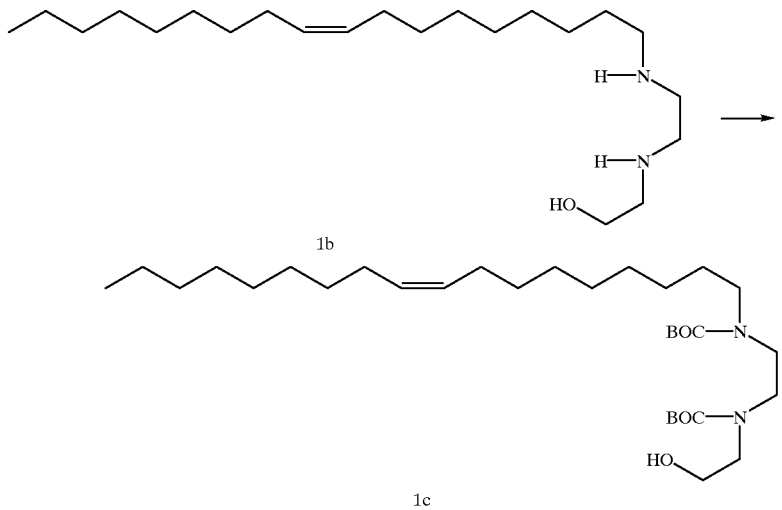

1b

1c

To a solution of crude N-(2-hydroxyethyl)-N'-oleyl-ethylenediamine (1b, 8.41 g) in $CH_2Cl_2$ (80 mL), (t-Boc)$_2$O (12.5 g, 57.3 mmol) was added dropwise. The reaction mixture was stirred at room temperature overnight, and then washed with $H_2O$, NaCl solution and dried over $MgSO_4$. The solvent was evaporated under reduced pressure and the residue was purified by column chromatography ($SiO_2$, EtOAc/Hexanes, 0~15%) to produce 5.63 g (50.0%) of product N,N'-di-t-Boc-N-(2-hydroxyethyl)-N'-oleyl-ethylenediamine, 1c. $^1$H NMR (CDCl$_3$): δ0.88 (t, J=7, 3H), 1.28 (m, 22H), 1.45 (s, 9H), 1.48 (s, 9H), 1.50 (m, 2H), 2.00 (m 4H), 3.19 (m, 2H), 3.36 (m, 6H), 3.75 (m, 2H), 5.35 (m, 2H).

1.4 compound 1d

At 0° C., oleyl chloride (4.5 g, 85%, 16.63 mmol) was added dropwise to a mixture of 1c above (6.36 g, 11.48 mmol) and Et$_3$N (2.4 mL, 17 mmol) in $CH_2Cl_2$ (50 mL). The reaction mixture was stirred at 0° C. for 3 h and room temperature overnight, and then diluted with $Et_2O$ (100 mL), washed with $H_2O$ (30 mL), 5% citric acid (30 mL), $H_2O$ (2×30 mL), NaHCO$_3$ (30 mL), NaCl solution (30 mL) and dried over $MgSO_4$. The solvent was evaporated under reduced pressure and the residue was purified on a silica gel column (EtOAc/hexanes, 0~5%) to give 9.03 g (96.2%) of product 1d. $^1$H NMR (CDCl$_3$): δ0.89 (m, 6H), 1.28 (m, 42H), 1.47 (s, 18H), 1.50 (m, 2H), 1.60 (m, 2H), 200 (m, 8H), 2.30 (t, J=7, 2H), 3.16 (m, 2H), 3.32 (m, 4H), 3.46 (m, 2H), 4.16 (M, 2H), 5.35 (m, 4H).

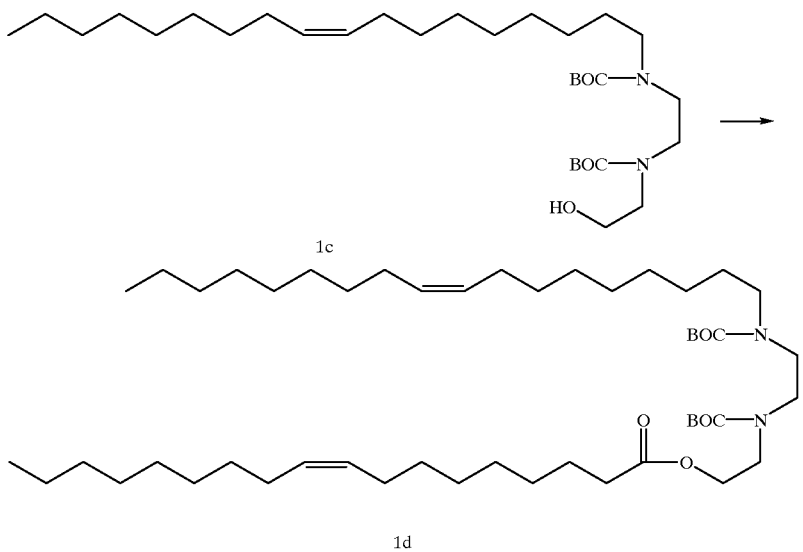

1c

1d 1.5 compound 1e

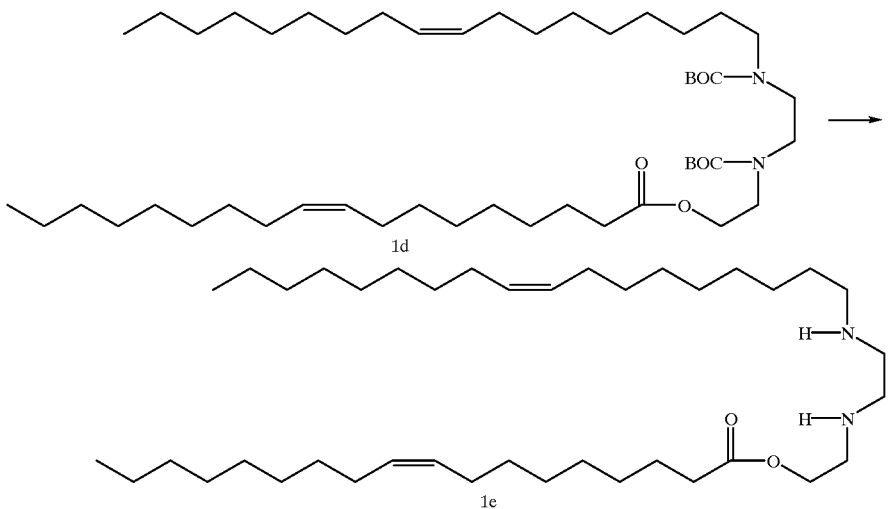

A mixture of compound 1d above (8 g, 9.78 mmol) and 4N HCl/dioxane (32 mL) was stirred at room temperature for 6 h and then filtered. The white solid was washed with hexanes (3×10 mL) and dried under vacuum to give 6.63 g (98.1%) of product 1e. mp 180~188° C. $^1$H NMR (CDCl$_3$): δ0.89. (m, 6H), 1.28 (m, 42H), 1.62 (m, 2H), 1.86 (m, 2H), 2.00 (m, 8H), 2.46 (t, J=7, 2H), 3.03 (m, 2H), 3.42 (m, 2H), 3.59 (m, 2H), 3.67 (m 2H), 4.47 (m, 2H), 5.35 (m, 4H).

1.6 Compound 1 for $C_{40}H_{77}N_2OCl$. 13/4 $H_2O$: C, 71.86; H, 12.05; N, 4.19; Cl, 5.31. Found: C, 71.77; H, 11.97; N, 4.14; Cl, 5.83.

Example 2

This example illustrates the generality of the synthetic method of set forth in FIG. 1. Using this synthetic route, a wide range of compounds of the invention having diverse hydrocarbon substituents attached to the 5-membered heterocyclic ring can be synthesized. The fatty acid chains utilized in this example are displayed below.

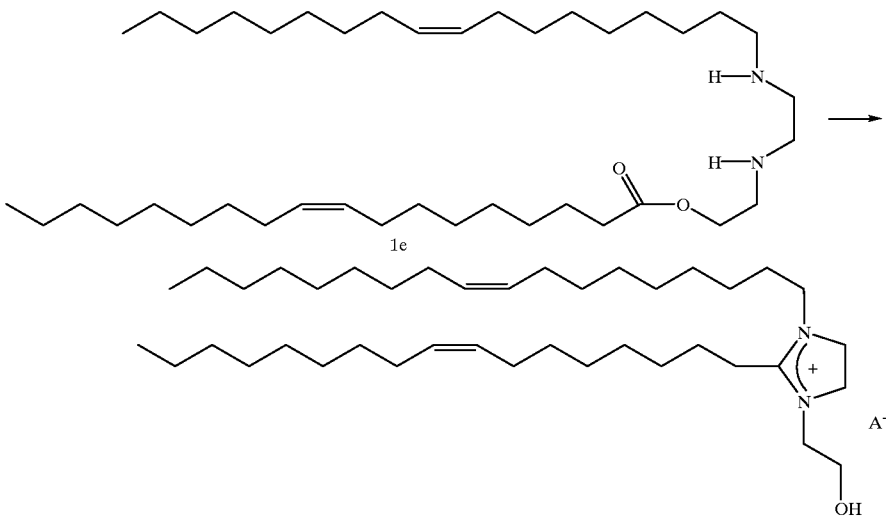

A suspension of 1e above (2.0 g, 2.89 mmol) in ethylene glycol (10 mL) was stirred at 150° C. for 1.5 h. After cooling to room temperature, the mixture was diluted with CH$_2$Cl$_2$ (100 mL), washed with MeOH/saturated NaCl (1:1, 3×30 mL), NaCl solution, and dried over MgSO$_4$. Evaporation and column chromatography (SiO$_2$, EtOAc/Hexanes 0~40%, MeOH/EtOAc 0~5%, MeOH/CH$_2$Cl$_2$ 0~5%) gave Compound 1 (0.88 g, 47.8%) as white wax. $^1$H NMR (CDCl$_3$): δ0.89 (m, 6H), 1.28 (m, 42H), 1.52 (m, 2H), 1.57 (m, 2H), 2.02 (m, 8H), 2.75 (m, 2H), 3.44 (m, 2H), 3.49 (m, 2H), 3.87 (m, 2H), 4.06 (m, 4H), 5.35 (m, 4H). Anal. Calcd 2.1 Synthesis of Alkyl Methansulfonate To a mixture of alkyl alcohol (37.2 mmol) and pyridine (13.4 mL) in CH$_2$Cl$_2$ (150 mL) was added MeSo$_2$Cl (4.35 mL, 56.2 mmol) over 40 min. The mixture was stirred at 0° C. for 40 minutes and then at room temperature for 4 h. Ice/H$_2$O (60 mL) and Et$_2$O (100 mL) were added. The organic layer was removed, washed with 0.5 N HCl (2×100 mL), H$_2$O (100 mL), 0.5 N NaHCO$_3$ (2×50 mL), H$_2$O (50 mL) and NaCl (50 mL). The organic layer was then dried over MgSO$_4$. The solvent was removed by evaporation affording the pure methanesulfonate. Yields and analytical data for the compounds synthesized are provided below.

2.1a. Dodecanyl methansulfonate: Yield, 94%. $^1$H NMR (CDCl$_3$): 0.88 (t, j=7, 3H), 1.26 (m, 18H), 1.75 (m, 2H), 3.01 (s, 3H), 4.26 (t, j=7, 2H).

2.1b. Tetradecanyl methanesulfonate: Yield 95%. $^1$H NMR (CDCl$_3$): 0.88 (t, j=7, 3H), 1.26 (m, 22H), 1.75 (m, 2H), 3.00 (s, 3H), 4.22 (t, j=7, 2H).

2.1c. Hexadecanyl methansulfonate: Yield 93%. $^1$H NMR (CDCl$_3$): 0.88 (t, j=7, 3H), 1.26 (m, 26H), 1.75 (m, 2H), 3.00 (s, 3H), 4.22 (t, j=7, 2H).

2.1d Octadecanyl methansulfonate: Yield 91%. $^1$H NMR (CDCl$_3$): 0.89 (t, j=7, 3H), 1.27 (m, 30H), 1.75 (m, 2H), 3.01 (s, 3H), 4.23 (t, j=7, 2H).

2.2 Synthesis of N-(2-hydroxyethyl)-N'-alkylethylenediamine

A stirred mixture of alkyl methanesulfonate (20.3 mmol) and 2-(2-aminoethylamino)ethanol (21.81 g, 209.7 mmol) was heated at 50° C. for 1.5 h. After cooling to room temperature, 10% NaOH, (30 mL) was added. The mixture was stirred for 30 min. then extracted with Et2O (100 mL). The Et$_2$O solution was washed with H$_2$O (3×50 mL) and NaCl. The organic layer was dried (MgSO$_4$) and the solvent was removed by evaporation. The crude product was used without any further purification.

2.3 Synthesis of N,N'-di-t-Boc-N-(2-hydroxyethyl)-N'-alkylethylenediamine

To a solution of N-(2-hydroxyethyl)-N'-alkylethylenediamine in CH2Cl2 (80 mL) was added (t-Boc)2O (12.5 g, 57.3 mmol) dropwise. After stirring at room temperature overnight, the mixture was washed with H$_2$O and NaCl. The organic layer was dried over MgSO$_4$. The solvent was removed by evaporation and the residue was purified by column chromatography (SiO$_2$, EtOAc/hexanes, 0–15%) giving the N-t-Boc products.

2.3a. Dodecanyl derivative: Yield 51% (2 steps). $^1$H NMR (CDCl$_3$): 0.86 (t, j=7, 3H), 1.25 (m, 22H), 1.44 (s, 9H), 1.47 (s, 9H), 1.51 (m, 2H), 3.17 (m, 2H), 3.37 (m, 6H), 3.73 (m, 2H).

2.3b. Tetradecanyl derivative: Yield 46% (2 steps). $^1$H NMR (CDCl$_3$): 0.88 (t, j=7, 3H), 1.25 (m, 22H), 1.44 (s, 9H), 1.47 (s, 9H), 1.51 (m, 2H), 3.17 (m, 2H), 3.37 (m, 6H), 3.73 (m, 2H).

2.3c. Hexadecanyl derivative: Yield 45% (2 steps). $^1$H NMR (CDCl$_3$): 0.87 (t, j=7, 3H), 1.25 (m, 26H), 1.44 (s, 9H), 1.47 (s, 9H), 1.51 (m, 2H), 3.16 (m, 2H), 3.36 (m, 6H), 3.72 (m, 2H).

2.3 d. Octadecanyl derivative: Yield 51% (2 steps). $^1$H NMR (CDCl$_3$): 0.87 (t, j=7, 3H), 1.25 (m, 30H), 1.44 (s, 9H), 1.46 (s, 9H), 1.51 (m, 2H), 3.17 (m, 2H), 3.37 (m, 6H), 3.73 (m, 2H).

2.4 Acylation of derivatives from 2.3

At 0° C., to a mixture of the t-Boc protected diamines (11.48 mmol) and Et$_3$N (2.4 mL) in CH$_2$Cl$_2$ (50 mL), the desired acid chloride (12.63 mmol, 1.1 eq.) was added dropwise. After stirring at 0° C. for 3 h and then at room temperature overnight, the mixture was diluted with Et2O (100 mL), washed with H$_2$O (30 mL), 5% citric acid (30 mL), H$_2$O (2×30 mL), NaHCO3 (30 mL) and NaCl (30 ml). The organic layer was dried (MgSO$_4$) and the solvent was removed by evaporation. The compounds were purified by column chromatography (SiO$_2$, EtOAc/hexanes, 0–5%).

2.4a. Dodecanyl derivative: Yield: 76%. $^1$H NMR (CDCl$_3$): 0.88 (m, 6H), 1.26 (m, 34H), 1.46 (s, 18H), 1.51 (m, 2H), 1.61 (m, 2H), 2.30 (t, j=7, 2H) 3.16 (m,2H), 3.31 (m, 4H), 3.46 (m, 2H), 4.16 (m, 2H).

2.4b. Tetradecanyl derivative: Yield 77%. $^1$H NM (CDCl$_3$): 0.88 (m, 6H), 1.26 (m, 42H), 1.46 (s, 18H), 1.51 (m, 2H), 1.61 (m, 2H), 2.30 (t, j=7, 2H) 3.16 (m, 2H), 3.31 (m, 4H), 3.46 (m, 2H), 4.16 (m, 2H)

2.4c. Hexadecanyl derivative: Yield 54%. $^1$H NMR (CDCl$_3$): 0.88 (m, 6H), 1.26 (m, 50H), 1.46 (s, 18H), 1.51 (m, 2H), 1.61 (m, 2H0), 2.30 (t, j=7, 2H), 3.46 (m, 2H), 4.16 (m, 2H).

2.4d. Octadecanyl derivative: Yield 57%. $^1$H NMR (CDCl$_3$): 0.88 (m, 6H), 1.26 (m, 58H), 1.46 (s, 18H), 1.46 (s, 18H), 1.51 (m, 2H), 1.61 (m, 2H), 2.30 (t, j=7, 2H), 3.16 (m, 2H), 3.31 (m, 4H), 3.46 (m, 2H), 4.16 (m, 2H).

2.5 Removal of t-Boc protecting groups

A mixture of a t-Boc protected acylated diamines and 4 N HCl in dioxane (32 mL) was stirred at room temperature for 6 h then filtered. The white solid was washed with hexanes (3×10 mL) and dried under vacuum to produce the diamine dihydrochloride.

2.5a. Dodecanyl derivative: Yield 93%, MP 188–193° C. $^1$H NMR (CDCl$_3$+MeOD): 0.89 (m, 6H), 1.26 (m, 34H), 1.61 (m, 2H), 1.71 (m, 2H), 2.44 (t, j=7, 2H) 3.03 (m, 2H), 3.44 (m, 6H), 4.39 (m, 2H).

2.5b. Tetradecanyl derivative: Yield 93%, MP 200–204° C. $^1$H NMR (CDCl$_3$+D$_2$O): 0.88 (m, 6H), 1.26 (m, 42H), 1.61 (m, 2H), 1.71 (m, 2H), 2.44 (t, j=7, 2H), 3.03 (m, 2H), 3.44 (m, 6H), 4.25 (m, 2H).

2.5c. Hexadecanyl derivative: Yield 92%, MP 208–211° C.: Insoluble in $^1$H NMR solvents.

2.5d. Octadecanyl derivative: Yield 82%, MP 211–216° C.: Insoluble in $^1$H NMR solvents.

2.6 Cyclization

A suspension of the diamine dihydrochloride (2.0 g) in ethylene glycol (10 mL) was heated to 150° C., with stirring for 1.5 h. After cooling to room temperature, the mixture was diluted with CH$_2$Cl$_2$ (100 mL), washed with MeOH/ saturated NaCl (1:1, 3× 30 mL), NaCl and the organic layer was dried (MgSO$_4$). The solvent was evaporated and the compounds were purified by column chromatography (SiO$_2$, EtOAc/hexanes, 0–40%, MeOH/EtOAc, 0–5%, MeOH/ CH$_2$Cl$_2$, 0–5%).

2.6a. Dodecanyl derivative: Yield 40%, white wax $^1$H NMR (CDCl$_3$): 0.88 (m, 6H), 1.26 (m, 34H), 1.53 (m, 2H), 1.61 (m, 2H), 2.75 (m, 2H), 3.43 (m, 2H), 3.49 (m, 2H), 3.86 (m, 2H), 4.06 (m, 2H). Anal. C$_{28}$H$_{57}$N$_2$OCl (1.5 H$_2$O): Theory C(67.27), H(12.01), N(5.60), Cl(7.11); Found C(67.40), H(11.98), N(5.67), Cl(7.37).

2.6b. Tetradecanyl derivative: Yield 35%, white wax. $^1$H NMR (CDCl$_3$): 0.88 (m, 6H), 1.26 (m, 42H), 1.56 (m, 2H), 1.66 (m, 2H), 2.74 (m, 2H), 3.43 (m, 2H), 3.49 (m, 2H), 3.86 (m, 2H), 4.06 (m, 4H). Anal. C$_{32}$H$_{65}$N$_2$OCl(H$_2$O): Theory: C(70.26), H(12.26), N(5.12), Cl(6.50); Found C(70.06), H(12.27), N(5.18), Cl(6.58).

2.6c. Hexadecanyl derivative: Yield 27%, white wax. $^1$H NMR (CDCl$_3$): 0.88 (m, 6H), 1.26 (m, 50H), 1.56 (m, 2H), 1.67 (m, 2H), 2.76 (m, 2H), 3.44 (m, 2H), 3.50 (m, 2H), 3.87 (m, 2H), 4.06 (m, 4H). Anal. C$_{36}$H$_{73}$N$_2$OCl(3/5H$_2$O): Theroy: C(72.57), H(12.46), N(4.70), Cl(5.96); Found C(72.57), H(12.59), N(4.67), Cl(6.03).

2.6d. Octadecanyl derivative: Yield 33%, white wax. $^1$H NMR (CDCl$_3$): 0.87 (m, 6H), 1.25 (m, 58H), 1.55 (m, 2H), 1.66 (m, 2H), 2.74 (m, 2H), 3.43 (m, 2H), 3.49 (m, 2H), 3.86 (m, 2H), 4.06 (m, 4H). Anal. C$_{40}$H$_{81}$N$_2$OCl(H$_2$O) Theory C(72.89), H(12.60), N(4.25), Cl(5.39); Found C(72.87), H(12.59), N(4.25), Cl(5.67).

Example 3

This example illustrates the derivatization of the free alcoholic hydroxyl group present in the certain of the compounds of the invention. This derivatization proceeds as displayed in Scheme 1.

Briefly, the final cyclized product is reacted with methane sulfonate to afford a reactive intermediate. This intermediate is then reacted with an amine, such as ethanolamine to provide derivatives analogous to that shown in Scheme 1.

Scheme 1

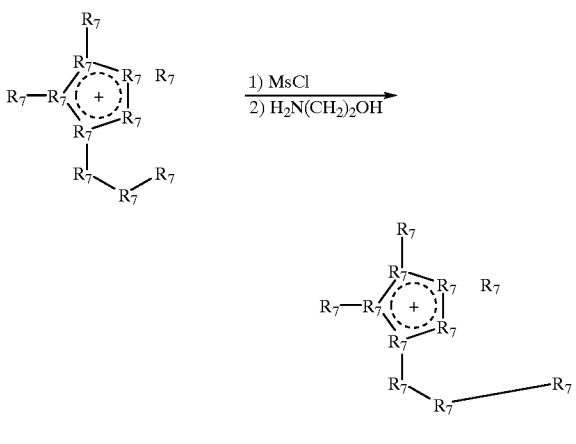

Example 4

This example provides an evaluation of the cationic lipid prepared in Example 1.

Experimental Protocol

Two mice studies have been performed for the evaluation of cationic lipids of the present invention, in comparison with DOTIM (see, Liu, et al., *Nature Biotechnology* 15:167–173 (1997)). In brief, the lipid combinations were tested as carriers for gene transfer by intravenous delivery in ICR female mice (25 g), and expression was determined using the plasmid p4119 containing the CAT reporter gene under the control of the HCMV promoter. The lipids were dissolved in a mixture of chloroform and methanol (1:1). Lipid films of cationic and neutral lipid (either cholesterol or DLPE) at a 1:1 molar ratio were formed with a rotary evaporator. The films were hydrated with 5% dextrose in water (D5W) at room temperature and extruded through a series of membranes having pore sizes of 400 nm, 200 nm, and 50 nm.

DNA-liposome complexes were prepared at a 1:6 DNA-:cationic lipid ratio (mg DNA per $\mu$mole cationic lipid) by adding the DNA, in a solution at 0.625 mg/mL concentration in D5W to the solution of liposomes, in an equal volume, with constant stirring, using a Hamilton Dilutor 540B (Hamilton, Reno, Nev.). DOTIM:cholesterol was used at a 1:6 DNA:cationic lipid ratio. The DNA solution was 0.3125 mg/mL DNA in D5W. The resulting complexes were sized using a Submicron Particle Sizer 370 (Nicomp, Santa Barbara, Calif.). Zeta potential was determined by a Zeta Plus, Zeta Potential Analyzer (Brookhaven Instrurtents Corp.). A total of 5 mice were tested per group. A dose of 62.5 $\mu$g p4119 plasmid DNA in 200 $\mu$L D5W was injected by tail vein per mouse. The lungs were harvested after 24 hours and assayed for CAT protein by ELISA assay. Each organ was homogenized in 1.0 mL of 5 mM EDTA/0.25M Tris-HCl pH 7.8 containing 5 $\mu$g/mL Aprotinin (Boehringer Mannheim, Indianapolis, Ind.), 5 $\mu$g/mL Leupeptin (Boehringer Mannheim, Indianapolis, Ind.), and 5 mM PMSF (Boehringer Mannheim, Indianapolis, Ind.). The resulting extracts were centrifuged and aliquots of the supernatant were removed for protein analysis, utilizing a bicinchoninic acid based reagent kit (Pierce, Rockford, Ill.). The remaining supernatant was heat treated at 65° C. for 15 min. The CAT activity assay was performed using 5 $\mu$L of heat treated supernatant, 25 $\mu$L of 125 $\mu$g/mL n-Butyryl CoA (Sigma, St. Louis, Mo.), 50 $\mu$L of 5 $\mu$Ci/mL $^{14}$C-chloramphenicol (DuPont NEN, Boston, Mass. ) and 50 $\mu$L of 0.25 M Tris-HCl/5 mM EDTA. Samples were incubated at 37° C. for 2 h. An addition of 300 $\mu$L of mixed xylenes (Aldrich, Milwaukee, Wis.) was made followed by vortexing and centrifugation at 14K rpm for 5 min. The xylene layer was then transferred into 750 $\mu$L of 0.25 M Tris-HCl/5 mM EDTA, vortexed, and centrifuged at 14K rpm for 5 min. The upper organic phase was then transferred into scintillation vials containing 5 mL of Ready Safe Liquid Scintillation Cocktail (Beckman, Fullerton, Calif.). Samples were counted for 1 min each.

Results

Results for evaluation of Compound 1, Compound 2, and DOTIM versus control (D5W) are provided in Table 1.

TABLE 1

| Composition | DNA/Lipid Ratio | Number Expressed |
| --- | --- | --- |
| D5W (Control) | 1:6 | 0/2 |
| DOTIM/CHOL | 1:6 | 5/5 |
| Compound 1/CHOL | 1:6 | 5/5 |
| Compound 1/DLPE | 1:6 | 3/5 |
| Compound 2/CHOL | 1:6 | 0/5 |

Compound 1/Chol showed similar lung CAT expression (2693.94 pg CAT/mg soluble protein) compared to that of DOTIM/Chol (2072.15 pg CAT/mg soluble protein). However, in a repeated protocol, the lung expression of Compound 1/Chol was 400.22 pg CAT/mg soluble protein. This difference may be due to the variation among different animal studies. These results indicate that Compound 1 retained the in vivo activity of DOTIM.

Both cholesterol and DLPE were used as additional lipids in the mice protocols since both have previously been shown to be useful helper lipids for delivery to lung endothelium by IV delivery. Compound 1/Chol compositions showed better activity than Compound 1/DLPE in both protocols. Therefore, for IV administration, cholesterol is the preferred helper lipid for Compound 1.

Compound 2 is the stearoyl derivative of DOTIM, which contains no double bond. No significant lung expression was observed for Compound 2/Chol in mice, indicating that the double bonds of oleoyl derivatives can increase the in vivo activity.

Example 3

This example provides an evaluation of Compound 1 as a suitable lipid in DNA:lipid complexes for transfection in rabbits.

3.1 Protocol

Pilot studies were conducted to assess the suitability of rabbits as a development model for delivery of lipid:DNA complexes. The study confirmed that rabbits offer the ability to express transfected genes as well as display some anticipated toxicity endpoints. Under suitable conditions, the rabbit was found to develop a dose-responsive vascular leak syndrome with the added advantage of expressing the CAT reporter protein. The lung was found to be the target organ for the complexes following IV delivery.

3.1a. Dosing for evaluation of Compound 1

A dosing scheme for 4 rabbits is provided in Table 2.

TABLE 2

| Rabbit | Material | Dose | Route/Delivery |
| --- | --- | --- | --- |
| 1 | Compound 1/CAT | 2.0 mg/kg | IV/0.5 mL/min |
| 2 | Compound 1/CAT | 1.5 mg/kg | IV/0.5 mL/min |
| 3 | Compound 1/CAT | 0.5 mg/kg | IV/0.5 mL/min |
| 4 | Compound 1 | highest vol. | IV/0.5 mL/kg |

A 2 mL blood sample is collected immediately prior to dose delivery for serum collection and another 2 mL for a CBC/clinical chemistry screen. Sufficient blood is also collected at necropsy to perform a CBC and clinical chemistry screen and preserve serum (minimum of 8 mL).

Approximately 24 hours after dosing the animals are euthanized using a barbiturate overdose. Following euthanasia, body weights are determined and an examination is made for the presence of pleural fluid. Any fluid present is harvested while avoiding blood contamination. Total protein and albumin levels are determined on the pleural fluid.

Tissues are collected and preserved as follows: lung tissue (8 vials in liquid nitrogen, 2 lobes infused with formalin, and optionally 2 Whirlpaks® in dry ice); liver tissue (multiple sites in formalin); kidney tissue (multiple sites in formalin); spleen tissue (multiple sites in formalin); heart tissue (multiple sites in formalin); and multiple serum samples (6 mL minimum in dry ice).

3.2 Results

Animals received the doses provided in Table 2 with no indication of distress. No lesions were noted in animals receiving just the lipid (Compound 1). The animal receiving just the lipid had diffusely red lungs which failed to collapse and no airway foam or excessive pleural fluid was noted. Very scant (normal) levels of pleural fluid were present in all animals. Small amounts of this fluid were collected from rabbits #1 and #3 for routine protein determinations.

Example 4

The compound of Formula III (Compound 2) was compared to Compound 1 for the ability to transfect lung cells according to the methods described in Example 2. Both compounds were formulated with cholesterol as the neutral lipid and plasmid p4119, and complexes injected IV into five mice each as described in Example 2. The CAT ELISA showed a mean CAT expression level of 853.20 (pg/mg) (+/−571.52) for Compound 2, compared to a mean of 306.09 (pg/mg) (+/−252.610 for Compound 1.

CAT ELISA (pg/mg or mL) for each of the rabbits was as follows: Rabbit #1, 10244.7 lung and 6665.9 serum; Rabbit #2, 963.8 lung and 1637.1 serum; Rabbit #3, 88.5 lung and 0 serum; Rabbit #4, 0 lung and 0 serum.

While the invention has been described in the foregoing description, the same is to be considered as illustrative and not restrictive in character. It is to be understood that only the preferred embodiments have been described and that all changes and modifications that come within the spirit of the invention are desired to be covered.

What is claimed is:

1. A method for introducing a nucleic acid into a mammalian cell, said method comprising contacting said cell with a composition comprising a nucleic acid and a compound having the formula:

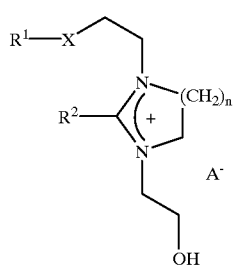

(I)

wherein $R^1$ and $R^2$ each independently represent a $C_8$–$C_{24}$ saturated or unsaturated hydrocarbon chain, uninterrupted or interrupted by from 1 to 3 heteroatom moieties selected from the group consisting of —O—, —S—, —NH— and —NR—;

X represents a member selected from the group consisting of —CH$_2$—, —O—, —S—, —NH— and —NR—;
wherein R is a lower alkyl group having from 1 to 4 carbon atoms;

n is an integer of from 1 to 2; and

A$^-$ is an anion.

2. A method in accordance with claim 1, wherein $R^1$ and $R^2$ each independently represent a $C_8$–$C_{24}$ saturated or unsaturated hydrocarbon chain.

3. A method in accordance with claim 1, wherein $R^1$ and $R^2$ each independently represent a $C_{12}$–$C_{20}$ saturated hydrocarbon chain.

4. A method in accordance with claim 1, wherein $R^1$ and $R^2$ each independently represent a $C_{12}$–$C_{20}$ unsaturated hydrocarbon chain.

5. A method in accordance with claim 1, wherein n is 1.

6. A method in accordance with claim 1, wherein $R^1$ and $R^2$ each independently represent a $C_{12}$–$C_{16}$ unsaturated hydrocarbon chain, X is —O—, and n is 1.

7. A method in accordance with claim 1, wherein $R^1$ represents a $C_{18}$-unsaturated hydrocarbon chain, $R^2$ represents a $C_{17}$ unsaturated hydrocarbon chain, X is —O—, and n is 1.

8. A method in accordance with claim 1, wherein $R^1$ and $R^2$ each contain a single double bond in the cis orientation.

9. A method in accordance with claim 1, wherein said compound has the formula:

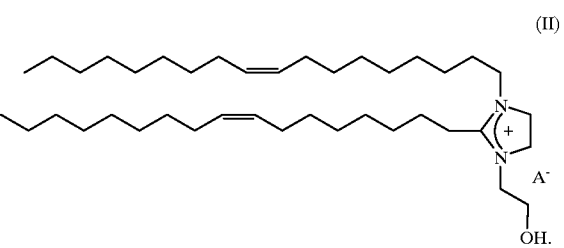

(II)

10. A method in accordance with claim 1, wherein said compound has the formula:

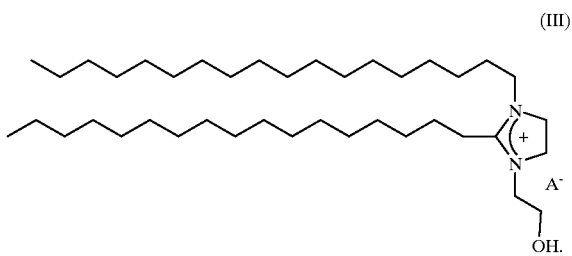

(III)

11. A method in accordance with claim 1, wherein said composition further comprises cholesterol.

12. A method in accordance with claim 1, wherein said composition further comprises dilauroylphosphatidylethanolamine.

13. A method in accordance with claim 1, wherein said composition is in the form of unilamellar vesicles.

14. A method in accordance with claim 1, wherein said nucleic acid is part of an expression cassette.

15. A method in accordance with claim 1, wherein said nucleic acid is complexed with liposomes comprising said compound.

16. A method in accordance with claim 1, wherein said nucleic acid encodes a therapeutic protein.

17. A method in accordance with claim 1, wherein said nucleic acid encodes a ribozyme.

* * * * *